United States Patent
Schwarz et al.

(10) Patent No.: US 10,233,773 B2
(45) Date of Patent: Mar. 19, 2019

(54) MONITORING SYSTEM FOR NON-FERROUS METAL PARTICLES

(71) Applicant: UNITED TECHNOLOGIES CORPORATION, Farmington, CT (US)

(72) Inventors: Frederick M. Schwarz, Glastonbury, CT (US); William G. Sheridan, Southington, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 523 days.

(21) Appl. No.: 14/943,418

(22) Filed: Nov. 17, 2015

(65) Prior Publication Data

US 2017/0138217 A1    May 18, 2017

(51) Int. Cl.
F01D 25/18    (2006.01)
F01D 21/10    (2006.01)
(Continued)

(52) U.S. Cl.
CPC ............. *F01D 21/10* (2013.01); *F01D 25/18* (2013.01); *F02C 3/10* (2013.01); *F02C 7/06* (2013.01); *F02C 7/36* (2013.01); *G01N 15/0656* (2013.01); *G01N 15/1031* (2013.01); *G01N 33/2858* (2013.01); *F05D 2220/32* (2013.01);
(Continued)

(58) Field of Classification Search
CPC . F01D 21/10; F01D 25/18; F02C 7/06; G01N 15/0656; G01N 15/1031; F05D 2260/98; F05D 2260/607
See application file for complete search history.

(56) References Cited

U.S. PATENT DOCUMENTS 2,258,792 A    4/1941 New
2,936,655 A    5/1960 Peterson et al.
(Continued)

FOREIGN PATENT DOCUMENTS

EP    0791383    8/1997
EP    1142850    10/2001
(Continued)

OTHER PUBLICATIONS

European Search Report for Application No. 16199358.9 dated Apr. 13, 2017.
(Continued)

*Primary Examiner* — Ehud Gartenberg
*Assistant Examiner* — James McGlynn
(74) *Attorney, Agent, or Firm* — Carlson, Gaskey & Olds, P.C.

(57) ABSTRACT

According to one aspect of the present disclosure, a debris monitoring system is disclosed that includes a fan, a geared architecture operatively coupled to the fan. The geared architecture includes a component having a non-ferrous metal coating. A scavenge pump is in fluid communication with the geared architecture via a lubrication sump. A non-ferrous chip detector is situated downstream of the geared architecture, but upstream of the scavenge pump. A controller is configured to determine a lubrication condition of the component based on a signal received from the non-ferrous chip detector, and command a status indicator in response thereto.

8 Claims, 7 Drawing Sheets

(51) Int. Cl.

| | | |
|---|---|---|
| F02C 3/10 | (2006.01) | |
| F02C 7/06 | (2006.01) | |
| F02C 7/36 | (2006.01) | |
| G01N 33/28 | (2006.01) | |
| G01N 15/06 | (2006.01) | |
| G01N 15/10 | (2006.01) | |
| G01N 15/00 | (2006.01) | |

(52) U.S. Cl.
CPC ............... F05D 2260/40311 (2013.01); F05D 2260/606 (2013.01); F05D 2260/607 (2013.01); F05D 2260/80 (2013.01); F05D 2260/83 (2013.01); F05D 2260/98 (2013.01); G01N 2015/0053 (2013.01); G01N 2015/1062 (2013.01); Y02T 50/675 (2013.01)

(56) References Cited

U.S. PATENT DOCUMENTS

| | | |
|---|---|---|
| 3,021,731 A | 2/1962 | Stoeckicht |
| 3,194,487 A | 7/1965 | Tyler et al. |
| 3,287,906 A | 11/1966 | McCormick |
| 3,352,178 A | 11/1967 | Lindgren et al. |
| 3,412,560 A | 11/1968 | Gaubatz |
| 3,641,550 A | 2/1972 | Lynas et al. |
| 3,747,343 A | 7/1973 | Rosen |
| 3,754,484 A | 8/1973 | Roberts |
| 3,820,719 A | 6/1974 | Clark |
| 3,892,358 A | 7/1975 | Gisslen |
| 3,932,058 A | 1/1976 | Harner et al. |
| 3,935,558 A | 1/1976 | Miller et al. |
| 3,988,889 A | 11/1976 | Chamay et al. |
| 4,130,872 A | 12/1978 | Harloff |
| 4,478,551 A | 10/1984 | Honeycutt, Jr. et al. |
| 4,649,114 A | 3/1987 | Miltenburger et al. |
| 4,696,156 A | 9/1987 | Burr et al. |
| 4,979,362 A | 12/1990 | Vershure, Jr. |
| 5,102,379 A | 4/1992 | Pagluica et al. |
| 5,141,400 A | 8/1992 | Murphy et al. |
| 5,315,243 A * | 5/1994 | Kempster ............ G01N 15/0656 324/204 |
| 5,317,877 A | 6/1994 | Stuart |
| 5,433,674 A | 7/1995 | Sheridan et al. |
| 5,447,411 A | 9/1995 | Curley et al. |
| 5,466,198 A | 11/1995 | McKibbin et al. |
| 5,524,847 A | 6/1996 | Brodell et al. |
| 5,544,700 A * | 8/1996 | Shagoury ................. F02C 7/14 165/139 |
| 5,610,341 A * | 3/1997 | Tortora ................... F01D 17/02 73/756 |
| 5,677,060 A | 10/1997 | Terentieva et al. |
| 5,760,298 A * | 6/1998 | Fisher ...................... G01F 1/64 324/453 |
| 5,778,659 A | 7/1998 | Duesler et al. |
| 5,857,836 A | 1/1999 | Stickler et al. |
| 5,915,917 A | 6/1999 | Eveker et al. |
| 5,975,841 A | 11/1999 | Lindemuth et al. |
| 5,985,470 A | 11/1999 | Spitsberg et al. |
| 6,223,616 B1 | 5/2001 | Sheridan |
| 6,297,626 B1 | 10/2001 | Boston et al. |
| 6,315,815 B1 | 11/2001 | Spadaccini et al. |
| 6,318,070 B1 | 11/2001 | Rey et al. |
| 6,387,456 B1 | 5/2002 | Eaton, Jr. et al. |
| 6,517,341 B1 | 2/2003 | Brun et al. |
| 6,588,934 B2 | 7/2003 | Law |
| 6,607,165 B1 | 8/2003 | Manteiga et al. |
| 6,709,492 B1 | 3/2004 | Spadaccini et al. |
| 6,814,541 B2 | 11/2004 | Evans et al. |
| 6,861,836 B2 | 3/2005 | Sammataro et al. |
| 7,021,042 B2 | 4/2006 | Law |
| 7,328,580 B2 | 2/2008 | Lee et al. |
| 7,374,403 B2 | 5/2008 | Decker et al. |
| 7,385,549 B2 | 6/2008 | Lovberg et al. |
| 7,591,754 B2 | 9/2009 | Duong et al. |
| 7,806,651 B2 | 10/2010 | Kennepohl et al. |
| 7,824,305 B2 | 11/2010 | Duong et al. |
| 7,886,875 B2 * | 2/2011 | Shevchencko .......... F01D 21/10 184/6.11 |
| 7,926,260 B2 | 4/2011 | Sheridan et al. |
| 7,997,868 B1 | 8/2011 | Liang et al. |
| 8,020,655 B2 | 9/2011 | Sheridan et al. |
| 8,037,626 B2 | 10/2011 | Moon et al. |
| 8,131,509 B2 * | 3/2012 | Novis ................ G05B 23/0229 702/185 |
| 8,205,432 B2 | 6/2012 | Sheridan |
| 8,226,822 B2 * | 7/2012 | Paradise ................. F01D 25/18 210/167.04 |
| 8,689,601 B2 | 4/2014 | Allam |
| 2008/0003096 A1 | 1/2008 | Kohli et al. |
| 2008/0317588 A1 | 12/2008 | Grabowski et al. |
| 2009/0056343 A1 | 3/2009 | Suciu et al. |
| 2010/0148396 A1 | 6/2010 | Xie et al. |
| 2010/0218483 A1 | 9/2010 | Smith |
| 2010/0331139 A1 | 12/2010 | McCune |
| 2011/0159797 A1 | 6/2011 | Beltman et al. |
| 2011/0293423 A1 | 12/2011 | Bunker et al. |
| 2012/0067671 A1 | 3/2012 | Sammataro et al. |
| 2012/0124964 A1 | 5/2012 | Hasel et al. |
| 2014/0141929 A1 * | 5/2014 | Hanlon .................... C25D 3/64 475/331 |
| 2016/0370275 A1 * | 12/2016 | Weiser .................. F16N 29/00 |
| 2017/0363529 A1 * | 12/2017 | Ture ................... G01N 15/0656 |

FOREIGN PATENT DOCUMENTS

| | | |
|---|---|---|
| EP | 1925855 | 5/2008 |
| EP | 2014877 | 1/2009 |
| GB | 1516041 | 6/1978 |
| GB | 2041090 | 9/1980 |
| GB | 2426792 | 12/2006 |
| WO | 2007038674 | 4/2007 |

OTHER PUBLICATIONS

Baker, R.W. (2000). Membrane technology and applications. New York, NY: McGraw-Hill. pp. 87-153.

Cheryan, M. (1998). Ultrafiltration and microfiltration handbook. Lancaster, PA: Tecnomic Publishing Company, Inc. pp. 171-236.

Seader, J.D. and Henley, E.J. (1998). Separation process principles. New York, NY: John Wiley & Sons, Inc. pp. 722-726 and 764-771.

Spadaccini, L.J., and Huang, H. (2002). On-line fuel deoxygenation for coke suppression. ASME, Jun. 2002. pp. 1-7.

Darrah, S. (1987). Jet fuel deoxygenation. Interim Report for Period Mar. 1987-Jul. 1988. pp. 1-22.

Bucknell, R.L. (1973). Influence of fuels and lubricants on turbine engine design and performance, fuel and lubircant analyses. Final Technical Report, Mar. 1971-Mar. 1973. pp. 1-252.

Hazlett, R.N. (1991). Thermal oxidation stability of aviation turbine fuels. Philadelphia, PA: ASTM. pp. 1-163.

Taylor, W.F. (1974). Deposit formation from deoxygenated hydrocarbons. I. General features. Ind. Eng. Chem., Prod. Res. Develop., vol. 13(2). 1974. pp. 133-138.

Taylor, W.F. (1974). Deposit formation from deoxygenated hydrocarbons. II. Effect of trace sulfur compounds. Ind. Eng. Chem., Prod. Res. Dev., vol. 15(1). 1974. pp. 64-68.

Taylor, W.F. and Frankenfeld, J.W. (1978). Deposit fromation from deoxygenated hydrocarbons. 3. Effects of trace nitrogen and oxygen compounds. Ind. Eng. Chem., Prod. Res. Dev., vol. 17(1). 1978. pp. 86-90.

Frankenfeld, J.W. and Taylor, W.F. (1980). Deposit fromation from deoxygenated hydrocarbons. 4. Studies in pure compound systems. Ind. Eng. Chem., Prod. Res. Dev., vol. 19(1). 1978. pp. 65-70.

Hemighaus, G., Boval, T., Bacha, J., Barnes, F., Franklin, M., Gibbs, L., . . . Morris, J. (2007). Aviation fuels: Techincal review. Chevron Products Company. pp. 1-94. Retrieved from: https://www.cgabusinessdesk.com/document/aviation_tech_review.pdf.

Spadaccini, L.J., Sobel, D.R., and Huang, H. (2001). Deposit formation and mitigation in aircraft fuels. Journal of Eng. for Gas Turbine and Power, vol. 123. Oct. 2001. pp. 741-746.

(56) References Cited

OTHER PUBLICATIONS

Edwards, T. and Zabarnick, S. (1993). Supercritical fuel deposition mechanisms. Ind. Eng. Chem. Res. vol. 32. 1993. pp. 3117-3122.
Huang, H., Sobel, D.R., and Spadaccini, L.J. (2002). Endothermic heat-sink of hydrocarbon fuels for scramjet cooling. AIAA/ASME/SAE/ASEE, Jul. 2002. pp. 1-7.
Bessarabov, D.G., Jacobs, E.P., Sanderson, R.D., and Beckman, I.N. (1996). Use of nonporous polymeric flat-sheet gas-separation membranes in a membrane-liquid contactor: experimental studies. Journal of Membrane Sciences, vol. 113. 1996. pp. 275-284.
Matsumoto, T., Toshiro, U., Kishida, A., Tsutomu, F., Maruyama, I., and Akashi, M. (1996). Novel functional polymers: Poly(dimethylsiloxane)-polyamide multiblock copolymer. VII. Oxygen permeability of aramid-silicone membranes in a gas-membrane-liquid system. Journal of Applied Polymer Science, vol. 64(6). May 9, 1997. pp. 1153-1159.
Technical Data. Teflon. WS Hampshire Inc. Retrieved from: http://catalog.wshampshire.com/Asset/psg_teflon_ptfe.pdf.
Anderson, N.E., Loewenthal, S.H., and Black, J.D. (1984). An analytical method to predict efficiency of aircraft gearboxes. NASA Technical Memorandum prepared for the Twentieth Joint Propulsion Conference. Cincinnati, OH. Jun. 11-13, 1984. pp. 1-25.
Edkins, D.P., Hirschkron, R., and Lee, R. (1972). TF34 turbofan quiet engine study. Final Report prepared for NASA. NASA-CR-120914. Jan. 1, 1972. pp. 1-99.
Waters, M.H. and Schairer, E.T. (1977). Analysis of turbofan propulsion system weight and dimensions. NASA Technical Memorandum. Jan. 1977. pp. 1-65.
Meyer, A.G. (1988). Transmission development of TEXTRON Lycoming's geared fan engine. Technical Paper. Oct. 1988. pp. 1-12.
Dudley, D.W., Ed. (1962). Gear handbook. New York, NY: McGraw-Hill. pp. 14-17 (TOC, Preface, and Index).
Hughes, C. (2002). Aerodynamic performance of scale-model turbofan outlet guide vanes designed for low noise. Prepared for the 40th Aerospace Sciences Meeting and Exhibit. Reno, NV. NASA/TM-2001-211352. Jan. 14-17, 2002. pp. 1-38.
Kaplan, B., Nicke, E, Voss, C. (2006), Design of a highly efficient low-noise fan for ultra-high bypass engines. Proceedings of GT2006 for ASME Turbo Expo 2006: Power for Land, Sea and Air. Barcelona, SP. May 8-11, 2006. pp. 1-10.
Gates, D. Bombardier flies at higher market. Seattle Times.
Decker, S. and Clough, R. (2016). GE wins shot at voiding pratt patent in jet-engine clash. Bloomberg Technology. Retrieved from: https://www.bloomberg.com/news/articles/2016-06-30/ge-wins-shot-to-invalidate-pratt-airplane-engine-patent-in-u-s.
Trembley, Jr., H.F. (1977). Determination of effects of ambient conditions on aircraft engine emissions. ALF 502 combustor rig testing and engine verification test. Prepared for Environmental Protection Agency. Sep. 1977. pp. 1-256.
Lewicki, D.G., Black, J.D., Savage, M., and Coy, J.J. (1985). Fatigue life analysis of a turboprop reduction gearbox. NASA Technical Memorandum. Prepared for the Design Technical Conference (ASME). Sep. 11-13, 1985. pp. 1-26.
Mccune, M.E. (1993). Initial test results of 40,000 horsepower fan drive gear system for advanced ducted propulsion systems. AIAA 29th Joint Conference and Exhibit. Jun. 28-30, 1993. pp. 1-10.
Wright, G.H. and Russell, J.G. (1990). The M.45SD-02 variable pitch geared fan engine demonstrator test and evaluation experience. Aeronautical Journal., vol. 84(836). Sep. 1980. pp. 268-277.
Drago, R.J. (1974). Heavy-lift helicopter brings up drive ideas. Power Transmission Design. Mar. 1987. pp. 1-15.
Krantz, T.L. (1990). Experimental and analytical evaluation of efficiency of helicopter planetary stage. NASA Technical Paper. Nov. 1990. pp. 1-19.
Honeywell LF507. Jane's Aero-engines, Aero-engines—Turbofan. Feb. 9, 2012.
Honeywell TFE731. Jane's Aero-engines, Aero-engines—Turbofan. Jul. 18, 2012.
NASA Conference Publication. Quiet, powered-lift propulsion. Cleveland, Ohio. Nov. 14-15, 1978. pp. 1-420.
"Civil Turbojet/Turbofan Specifications", Jet Engine Specification Database (Apr. 3, 2005).
Kandebo, S.W. (1993). Geared-turbofan engine design targets cost, complexity. Aviation Week & Space Technology, 148(8). Start p. 32.
Hendricks, E.S. and Tong, M.T. (2012). Performance and weight estimates for an advanced open rotor engine. NASA/TM-2012-217710. pp. 1-13.
Guynn, M. D., Berton, J.J., Fisher, K. L., Haller, W.J., Tong, M. T., and Thurman, D.R. (2011). Refined exploration of turbofan design options for an advanced single-aisle transport. NASA/TM-2011-216883. pp. 1-27.
Zalud, T. (1998). Gears put a new spin on turbofan performance. Machine Design, 70(20), p. 104.
Miller, J.L. and Kitaljevich, D. (2000). In-line oil debris monitor for aircraft engine condition assessment.
Muir, D. and Howe, B. (1996). In-line oil debris monitor (ODM) for the advanced tactical fighter engine. From Technology Showcase: Integrated Monitoring, Diagnostics, and Failure Prevention. Preceedings of a Joint Conference, Alabama: Mobile, Apr. 22-26, 1996.
Drago, R.J. and Margasahayam, R.N. (1987). Stress analysis of planet gears with integral bearings; 3D finite-element model development and test validation. 1987 MSC NASTRAN World Users Conference. Los Angeles, CA. Mar. 1987. pp. 1-14.
Savelle, S.A. and Garrard, G.D. (1996). Application of transient and dynamic simulations to the U.S. Army T55-L-712 helicopter engine. The American Society of Mechanical Engineers. Presented Jun. 10-13, 1996. pp. 1-8.
Kurzke, J. (2008). Preliminary Design, Aero-engine design: From state of the art turbofans towards innovative architectures. pp. 1-72.
Zamboni, G. and Xu, L. (2009). Fan root aerodynamics for large bypass gas turbine engines: Influence on the engine performance and 3D design. Proceedings of ASME Turbo Expo 2009: Power for Land, Sea and Air. Jun. 3-12, 2009, Orlando, Florida, USA. pp. 1-12.
Han, J., Dutta, S., and Ekkad, S.V. (2000). Gas turbine heat transfer and cooling technology. New York, NY: Taylor & Francis. pp. 1-25, 129-157, and 160-249.
Mattingly, J.D. (1996). Elements of gas turbine propulsion. New York, New York: McGraw-Hill, Inc. pp. 1-18, 60-62, 85-87, 95-104, 121-123, 223-234, 242-245, 278-280, 303-309, 323-326, 462-479, 517-520, 563-565, 673-675, 582-685, 697-699, 703-705, 802-805, 862-864, and 923-925.
Declaration of Reza Abhari, Ph.D. In re U.S. Pat. No. 8,844,265. Executed Jun. 28, 2016. pp. 1-91.
Declaration of John Eaton, Ph.D. In re U.S. Pat. No. 8,869,568. Executed Mar. 28, 2016. pp. 1-87.
Declaration of Reza Abhari. In re U.S. Pat. No. 8,695,920. Executed Nov. 30. pp. 1-67.
Declaration of Reza Abhari. In re U.S. Pat. No. 8,448,895. Executed Nov. 28. pp. 1-81.
Declaration of Reza Abhari. In re U.S. Pat. No. 8,695,920, claims 1-4, 7-14, 17 and 19. Executed Nov. 29. pp. 1-102.
Declaration of Dr. Magdy Attia. In re U.S. Pat. No. 8,313,280. Executed Oct. 21, 2016. pp. 1-88.
Lord, W.K., Macmartin, D.G., and Tillman, T.G. (2000). Flow control opportunities in gas turbine engines. American Institute of Aeronautics and Astronautics. pp. 1-15.
Daly, M. Ed. (2010). Jane's Aero-Engine. Issue Twenty-seven. Mar. 2010. p. 633-636.
Roux, E. (2007). Turbofan and turbojet engines database handbook. Editions Elodie Roux. Blagnac: France. pp. 1-595.
Wilfert, G. (2008). Geared fan. Aero-Engine Design: From State of the Art Turbofans Towards Innovative Architectures, von Karman Institute for Fluid Dynamics, Belgium, Mar. 3-7, 2008. pp. 1-26.
Declaration of Dr. Magdy Attia. In re U.S. Pat. No. 8,517,668. Executed Dec. 8, 2016. pp. 1-81.
Cramoisi, G. Ed. (2012). Death in the Potomac: The crash of Air Florida Flight 90. Air Crash Investigations. Accident Report NTSB/AAR-82-8. p. 45-47.

(56) References Cited

OTHER PUBLICATIONS

Norton, M. and Karczub, D. (2003). Fundamentals of noise and vibration analysis for engineers. Press Syndicate of the University of Cambridge. New York: New York. p. 524.
U.S. Department of Transportation: Federal Aviation Administration Advisory Circular. Runway overrun prevention. Dated: Nov. 6, 2007. p. 1-8 and Appendix 1 p. 1-15, Appendix 2 p. 1-6, Appendix 3 p. 1-3, and Appendix 4 p. 1-5.
U.S. Department of Transportation: Federal Aviation Administration Advisory Circular. Standard operating procedures for flight deck crewmembers. Dated: Feb. 27, 2003.. p. 1-6 and Appendices.
Heingartner, P., MBA, D., Brown, D. (2003). Determining power losses in the helical gear mesh; Case Study. ASME 2003 Design Engineering Technical Conferences. Chicago, IL. Sep. 2-6, 2003. pp. 1-7.
Vasudevan, A.K. and Petrovic, J.J. (1992). A comparative overview of molybedenum disilicide composites. Materials Science and Engineering, A155, 1992. pp. 1-17.
Clarke, D.R. and Levi, C.G. (2003). Materials design for the next generation thermal barrier coatings. Annual. Rev. Mater. Res. vol. 33. 2003. pp. 383-417.
Lee, K.N. (2000). Current status of environmental barrier coatings for Si-Based ceramics. Surface and Coatings Technology 133-134, 2000. pp. 1-7.
Bornstein, N. (1993). Oxidation of advanced intermetallic compounds. Journal de Physique IV, 1993, 03 (C9), pp. C9-367-C9-373.
Krenkel, W., Naslain, R., and Schneider, H. Eds. (2001). High temperature ceramic matrix composites pp. 224-229. Weinheim, DE: Wiley-VCH Verlag GmbH.
Gibala, R., Ghosh, A.K., Van Aken, D.C., Srolovitz, D.J., Basu, A., Chang, H., . . . Yang, W. (1992). Mechanical behavior and interface design of MoSi2-based alloys and composites. Materials Science and Engineering, A155, 1992. pp. 147-158.
Shah, D.M. (1992). MoSi2 and other silicides as high temperature structural materials. Superalloys 1992. The Minerals, Metals, & Materials Society. pp. 409-422.
Zhao, J.C. and Westbrook, J.H. (2003). Ultrahigh-temperature materials for jet engines. MRS Bulletin. vol. 28 (9). Sep. 2003. pp. 622-630.
Tsirlin, M., Pronin, Y.E., Florina, E.K.., Mukhametov, S. Kh., Khatsernov, M.A., Yun, H.M., . . . Kroke, E. (2001). Experimental investigation of multifunctional interphase coatings on SiC fibers for non-oxide high temperature resistant CMCs. High Temperature Ceramic Matrix Composites. 4th Int'l Conf. on High Temp. Ceramic Matrix Composites. Oct. 1-3, 2001. pp. 149-156.
Jacobson, N.S. (1993). Corrosion of silicon-based ceramics in combustion environments. J. Am. Ceram. Soc. 76 (1). pp. 3-28.
Jorgensen, P.J., Wadsworth, M.E., and Cutler, I.B. (1961). Effects of water vapor on oxidation of silicon carbide. J. Am. Ceram. Soc. 44(6). pp. 248-261.
Xu, Y., Cheng, L., Zhang, L., Ying, H., and Zhou, W. (1999). Oxidation behavior and mechanical properties of C/SiC composites with Si—MoSi2 oxidation protection coating. J. of Mat. Sci. vol. 34. 1999. pp. 6009-6014.
Sundaram, S.K., Hsu, J-Y., Speyer, R.F. (1995). Molten glass corrosion resistance of immersed combustion-heating tube materials in e-glass. J. Am. Ceram. Soc. 78(7). pp. 1940-1946.
Jeng, Y.-L., Lavernia, E.J. (1994). Processing of molybdenum disilicide. J. of Mat. Sci. vol. 29. 1994. pp. 2557-2571.
Suzuki, Y., Morgan, P.E.D., and Niihara, K. (1998). Improvement in mechanical properties of powder-processed MoSi2 by the addition of Sc2O3 and Y2O3. J. Am. Ceram. Soci. 81(12). pp. 3141-3149.
Webster, J.D., Westwood, M.E., Hayes, F.H., Day, R.J., Taylor, R., Duran, A., . . . Vogel, W.D. (1998). Oxidation protection coatings for C/SiC based on yttrium silicate. Journal of European Ceramic Society vol. 18. 1998. pp. 2345-2350.
Petrovic, J.J., Castro, R.G., Vaidya, R.U., Peters, M.I., Mendoza, D., Hoover, R.C., and Gallegos, D.E. (2001). Molybdenum disilicide materials for glass melting sensor sheaths. Ceramic Engineering and Science Proceedings. vol. 22(3). 2001. pp. 59-64.

Kahn, H., Tayebi, N., Ballarini, R., Mullen, R.L., Heuer, A.H. (2000). Fracture toughness of polysilicon MEMS devices. Sensors and Actuators vol. 82. 2000. pp. 274-280.
Muhlstein, C.L., Stach, E.A., and Ritchie, R.O. (2002). A reaction-layer mechanism for the delayed failure of micron-scale polycrystalline silicon structural films subjected to high-cycle fatigue loading. Acta Materialia vol. 50. 2002. pp. 3579-3595.
Sundaram, S.K., Hsu, J-Y., Speyer, R.F. (1994). Molten glass corrosion resistance of immersed combustion-heating tube materials in soda-lime-silicate glass. J. Am. Ceram. Soc. 77(6). pp. 1613-1623.
Leckie, F.A. and Dal Bello, D.J. (2009). Strength and stiffness of engineering systems. Mechanical Engineering Series. Springer. pp. 1-3.
El-Sayad, A.F. (2008). Aircraft propulsion and gas turbine engines. Boca Raton, FL: CRC Press. pp. 215-219 and 855-860.
Bunker, R.S. (2005). A review of shaped hole turbine film-cooling technology. Journal of Heat Transfer vol. 127. Apr. 2005. pp. 441-453.
Davies, D. and Miller, D.C. (1971). A variable pitch fan for an ultra quiet demonstrator engine. 1976 Spring Convention: Seeds for Success in Civil Aircraft Design in the Next Two Decades. pp. 1-18.
Middleton, P. (1971). 614: VFW's jet feederliner. Flight International, Nov. 4, 1971. p. 725, 729-732.
Schaefer, J.W., Sagerser, D.R., and Stakolich, E.G. (1977). Dynamics of high-bypass-engine thrust reversal using a variable-pitch fan. Technical Report prepare for NASA. NASA-TM-X-3524. May 1, 1977. pp. 1-33.
Mcmillian, A. (2008) Material development for fan blade containment casing. Abstract. p. 1. Conference on Engineering and Physics: Synergy for Success 2006. Journal of Physics: Conference Series vol. 105. London UK. Oct. 5, 2006.
Kurzke, J. (2009). Fundamental differences between conventional and geared turbofans. Proceedings of ASME Turbo Expo: Power for Land, Sea, and Air. 2009, Orlando, Florida. pp. 145-153.
Agarwal, B.D and Broutman, L.J. (1990). Analysis and performance of fiber composites, 2nd Edition. John Wiley & Sons, Inc. New York: New York. pp. 1-30, 50-51, 56-58, 60-61, 64-71, 87-89, 324-329, 436-437.
Carney, K., Pereira, M. Revilock, and Matheny, P. (2003). Jet engine fan blade containment using two alternate geometries. 4th European LS-DYNA Users Conference. pp. 1-10.
Brines, G.L. (1990). The turbofan of tomorrow. Mechanical Engineering: The Journal of the American Society of Mechanical Engineers, 108(8), 65-67.
Faghri, A. (1995). Heat pipe and science technology. Washington, D.C: Taylor & Francis. pp. 1-60.
Hess, C. (1998). Pratt & Whitney develops geared turbofan. Flug Revue 43(7). Oct. 1998.
Grady, J.E., Weir, D.S., Lamoureux, M.C., and Martinez, M.M. (2007). Engine noise research in NASA's quiet aircraft technology project. Papers from the International Symposium on Air Breathing Engines (ISABE). 2007.
Griffiths, B. (2005). Composite fan blade containment case. Modern Machine Shop. Retrieved from: http://www.mmsonline.com/articles/composite-fan-blade-containment-case pp. 1-4.
Hall, C.A. and Crichton, D. (2007). Engine design studies for a silent aircraft. Journal of Turbomachinery, 129, 479-487.
Haque, A. and Shamsuzzoha, M., Hussain, F., and Dean, D. (2003). S20-glass/epoxy polymer nanocomposites: Manufacturing, structures, thermal and mechanical properties. Journal of Composite Materials, 37 (20), 1821-1837.
Brennan, P.J. and Kroliczek, E.J. (1979). Heat pipe design handbook. Prepared for National Aeronautics and Space Administration by B & K Engineering, Inc. Jun. 1979. pp. 1-348.
Horikoshi, S. and Serpone, N. (2013). Introduction to nanoparticles. Microwaves in nanoparticle synthesis. Wiley-VCH Verlag GmbH & Co. KGaA. pp. 1-24.
Kerrebrock, J.L. (1977). Aircraft engines and gas turbines. Cambridge, MA: The MIT Press. p. 11.
Xie, M. (2008). Intelligent engine systems: Smart case system. NASA/CR-2008-215233. pp. 1-31.

(56) References Cited

OTHER PUBLICATIONS

Knip, Jr., G. (1987). Analysis of an advanced technology subsonic turbofan incorporating revolutionary materials. NASA Technical Memorandum. May 1987. pp. 1-23.

Willis, W.S. (1979). Quiet clean short-haul experimental engine (QCSEE) final report. NASA/CR-159473 pp. 1-289.

Kojima, Y., Usuki, A. Kawasumi, M., Okada, A., Fukushim, Y., Kurauchi, T., and Kamigaito, O. (1992). Mechanical properties of nylon 6-clay hybrid. Journal of Materials Research, 8(5), 1185-1189.

Kollar, L.P. and Springer, G.S. (2003). Mechanics of composite structures. Cambridge, UK: Cambridge University Press. p. 465.

Ramsden, J.M. (Ed). (1978). The new European airliner. Flight International, 113(3590). Jan. 7, 1978. pp. 39-43.

Langston, L. and Faghri, A. Heat pipe turbine vane cooling. Prepared for Advanced Turbine Systems Annual Program Review. Morgantown, West Virginia. Oct. 17-19, 1995. pp. 3-9.

Oates, G.C. (Ed). (1989). Aircraft propulsion systems and technology and design. Washington, D.C.: American Institute of Aeronautics, Inc. pp. 341-344.

Lau, K., Gu, C., and Hui, D. (2005). A critical review on nanotube and nanotube/nanoclay related polymer composite materials. Composites: Part B 37(2006) 425-436.

Shorter Oxford English dictionary, 6th Edition. (2007). vol. 2, N-Z. p. 1888.

Lynwander, P. (1983). Gear drive systems: Design and application. New York, New York: Marcel Dekker, Inc. pp. 145, 355-358.

Sweetman, B. and Sutton, O. (1998). Pratt & Whitney's surprise leap. Interavia Business & Technology, 53.621, p. 25.

Mattingly, J.D. (1996). Elements of gas turbine propulsion. New York, New York: McGraw-Hill, Inc. pp. 8-15.

Pyrograf-III Carbon Nanofiber. Product guide. Retrieved Dec. 1, 2015 from: http://pyrografproducts.com/Merchant5/merchant.mvc?Screen=cp_nanofiber.

Nanocor Technical Data for Epoxy Nanocomposites using Nanomer 1.30E Nanoclay. Nnacor, Inc. Oct. 2004.

Ratna, D. (2009). Handbook of thermoset resins. Shawbury, UK: iSmithers. pp. 187-216.

Wendus, B.E., Stark, D.F., Holler, R.P., and Funkhouser, M.E. (2003). Follow-on technology requirement study for advanced subsonic transport. NASA/CR-2003-212467. pp. 1-37.

Silverstein, C.C., Gottschlich, J.M., and Meininger, M. The feasibility of heat pipe turbine vane cooling. Presented at the International Gas Turbine and Aeroengine Congress and Exposition, The Hague, Netherlands. Jun. 13-16, 1994.pp. 1-7.

Merriam-Webster's collegiate dictionary, 11th Ed. (2009). p. 824.

Merriam-Webster's collegiate dictionary, 10th Ed. (2001). p. 1125-1126.

Whitaker, R. (1982). ALF 502: plugging the turbofan gap. Flight International, p. 237-241, Jan. 30, 1982.

Hughes, C. (2010). Geared turbofan technology. NASA Environmentally Responsible Aviation Project. Green Aviation Summit. NASA Ames Research Center. Sep. 8-9, 2010. pp. 1-8.

Gliebe, P.R. and Janardan, B.A. (2003). Ultra-high bypass engine aeroacoustic study. NASA/CR-2003-21252. GE Aircraft Engines, Cincinnati, Ohio. Oct. 2003. pp. 1-103.

Moxon, J. How to save fuel in tomorrow's engines. Flight International. Jul. 30, 1983. 3873(124). pp. 272-273.

File History for U.S. Appl. No. 12/131,876.

Cusick, M. (1981). Avco Lycoming's ALF 502 high bypass fan engine. Society of Automotive Engineers, inc. Business Aircraft Meeting & Exposition. Wichita, Kansas. Apr. 7-10, 1981. pp. 1-9.

Fledderjohn, K.R. (1983). The TFE731-5: Evolution of a decade of business jet service. SAE Technical Paper Series. Business Aircraft Meeting & Exposition. Wichita, Kansas. Apr. 12-15, 1983. pp. 1-12.

Dickey, T.A. and Dobak, E.R. (1972). The evolution and development status of ALF 502 turbofan engine. National Aerospace Engineering and Manufacturing Meeting. San Diego, California. Oct. 2-5, 1972. pp. 1-12.

Gunston, B. (Ed.) (2000). Jane's aero-engines, Issue seven. Coulsdon, Surrey, UK: Jane's Information Group Limited. pp. 510-512.

Ivchenko-Progress D-436. Jane's Aero-engines, Aero-engines—Turbofan. Feb. 8, 2012.

Ivchenko-Progress AI-727M. Jane's Aero-engines, Aero-engines—Turbofan. Nov. 27, 2011.

Ivchenko-Progress D-727. Jane's Aero-engines, Aero-engines—Turbofan. Feb. 7, 2007.

Turbomeca Aubisque. Jane's Aero-engines, Aero-engines—Turbofan. Nov. 2, 2009.

Aviadvigatel D-110. Jane's Aero-engines, Aero-engines—Turbofan. Jun. 1, 2010.

Rolls-Royce M45H. Jane's Aero-engines, Aero-engines—Turbofan. Feb. 24, 2010.

Honeywell LF502. Jane's Aero-engines, Aero-engines—Turbofan. Feb. 9, 2012.

* cited by examiner

MONITORING SYSTEM FOR NON-FERROUS METAL PARTICLES

BACKGROUND

This disclosure relates to lubrication, and more particularly to monitoring for non-ferrous metal particles in a flow of lubricant in a lubrication system.

A gas turbine engine typically includes a fan section, a compressor section, a combustor section and a turbine section. Air entering the compressor section is compressed and delivered into the combustion section where it is mixed with fuel and ignited to generate a high-speed exhaust gas flow. The high-speed exhaust gas flow expands through the turbine section to drive the compressor and the fan section.

A speed reduction device such as an epicyclical gear assembly may be utilized to drive the fan section such that the fan section may rotate at a speed different than the turbine section so as to increase the overall propulsive efficiency of the engine. In such engine architectures, a shaft driven by one of the turbine sections provides an input to the epicyclical gear assembly that drives the fan section at a reduced speed such that both the turbine section and the fan section can rotate at closer to optimal speeds. Such gear assemblies may include journal bearings which require lubrication.

SUMMARY

One example embodiment of a debris monitoring system includes a fan and a geared architecture that is operatively coupled to the fan. The geared architecture includes a component having a non-ferrous metal coating. A scavenge pump is in fluid communication with the geared architecture via a lubrication sump. A non-ferrous chip detector is situated downstream of the geared architecture, but upstream of the scavenge pump. A controller is configured to determine a lubrication condition of the component based on a signal received from the non-ferrous chip detector, and command a status indicator in response thereto.

In another example embodiment of the above described debris monitoring system, the component is a journal pin.

In another example embodiment of any of the above described debris monitoring systems, the non-ferrous metal coating comprises one or more of copper, silver, and lead.

In another example embodiment of any of the above described debris monitoring systems, wherein the non-ferrous chip detector is situated downstream of the lubrication sump.

In another example embodiment of any of the above described debris monitoring systems, the scavenge pump is operative to pump lubricant from the lubrication sump, and from one or more additional lubrication sumps that are located in parallel flow paths that omit the geared architecture.

In another example embodiment of any of the above described debris monitoring systems, the non-ferrous chip detector at least partially surrounds a portion of conduit that carries lubricant between the geared architecture and scavenge pump.

In another example embodiment of any of the above described debris monitoring systems, the portion of conduit is a bypass whose inlet and outlet are in fluid communication with a main conduit that also carries lubricant between the geared architecture and scavenge pump, the bypass having a smaller diameter than the main conduit.

In another example embodiment of any of the above described debris monitoring systems, a magnetic device is situated downstream of the geared architecture but upstream of the inlet to the bypass, and operative to divert ferrous particles away from the inlet.

In another example embodiment of any of the above described debris monitoring systems, the non-ferrous chip detector includes at least one field coil, a sense coil, and a sensor. The at least one field coil is configured to provide a magnetic field based on an oscillating input signal. The sense coil is spaced apart from, but inductively coupled to the at least one field coil, and is configured to provide an output signal based on the magnetic field. The sensor is electrically coupled to the sense coil, and is configured to detect a presence of non-ferrous particles in the conduit based on the output signal and a predefined signal profile of a non-ferrous metal particle.

In another example embodiment of any of the above described debris monitoring systems, the at least one field coil and the sense coil wrap circumferentially around the conduit.

In another example embodiment of any of the above described debris monitoring systems, the at least one field coil comprises a first field coil upstream of the sense coil, and a second field coil downstream of the sense coil.

One example embodiment of a method includes inductively sensing whether a threshold amount of non-ferrous metal debris is present in a flow of lubricant at a location in a lubrication system that is downstream of a geared architecture and upstream of a scavenge pump. The scavenge pump is in fluid communication with the geared architecture via a lubrication sump. The method also includes commanding a status indicator in response to the inductive sensing.

In another example embodiment of the above described method, the location is downstream of the lubrication sump.

In another example embodiment of any of the above described methods, the method includes diverting lubricant from a main conduit that carries lubricant between the geared architecture and scavenge pump into a bypass whose inlet and outlet are in fluid communication with the main conduit. The location at which the inductive sensing is performed is in the bypass.

In another example embodiment of any of the above described methods, the method includes providing a magnetic field downstream of the geared architecture but upstream of the inlet to the bypass, to divert ferrous particles away from the inlet.

In another example embodiment of any of the above described methods, the inductive sensing includes passing an oscillating input signal through at least one field coil to provide a magnetic field in the flow of lubricant at the location; obtaining an output signal based on the magnetic field from a sense coil that is spaced apart from, but inductively coupled to the at least one field coil; and analyzing the output signal to detect whether non-ferrous metal debris is present in the flow of lubricant at the location based on a predefined signal profile of a non-ferrous metal particle.

One example embodiment of a gas turbine engine includes a turbine operatively connected to a fan rotor through a geared architecture that provides a gear reduction. The geared architecture includes a component having a non-ferrous metal coating. A scavenge pump is in fluid communication with the geared architecture via a lubrication sump. A non-ferrous chip detector is situated downstream of the geared architecture, but upstream of the lubrication pump. A controller is configured to determine a lubrication condition of the component based on a signal received from the non-ferrous chip detector, and command a status indicator in response thereto.

In another example embodiment of the above described gas turbine engine, the component having a non-ferrous metal coating is a journal pin.

In another example embodiment of any of the above described methods, the non-ferrous chip detector at least partially surrounds a portion of conduit that carries lubricant between the geared architecture and scavenge pump; and the portion of conduit is a bypass whose inlet and outlet are in fluid communication with a main conduit that also carries lubricant between the geared architecture and scavenge pump, the bypass having a smaller diameter than the main conduit.

In another example embodiment of any of the above described methods, a magnetic device is situated downstream of the geared architecture but upstream of the inlet to the bypass, and is operative to divert ferrous particles away from the inlet.

The embodiments described above and herein may be taken independently or in any combination. Features described in connection with one embodiment are applicable to all embodiments, unless such features are incompatible. The features described above, and other features, may be best understood from the following drawings and specification.

DETAILED DESCRIPTION

Figure 1:
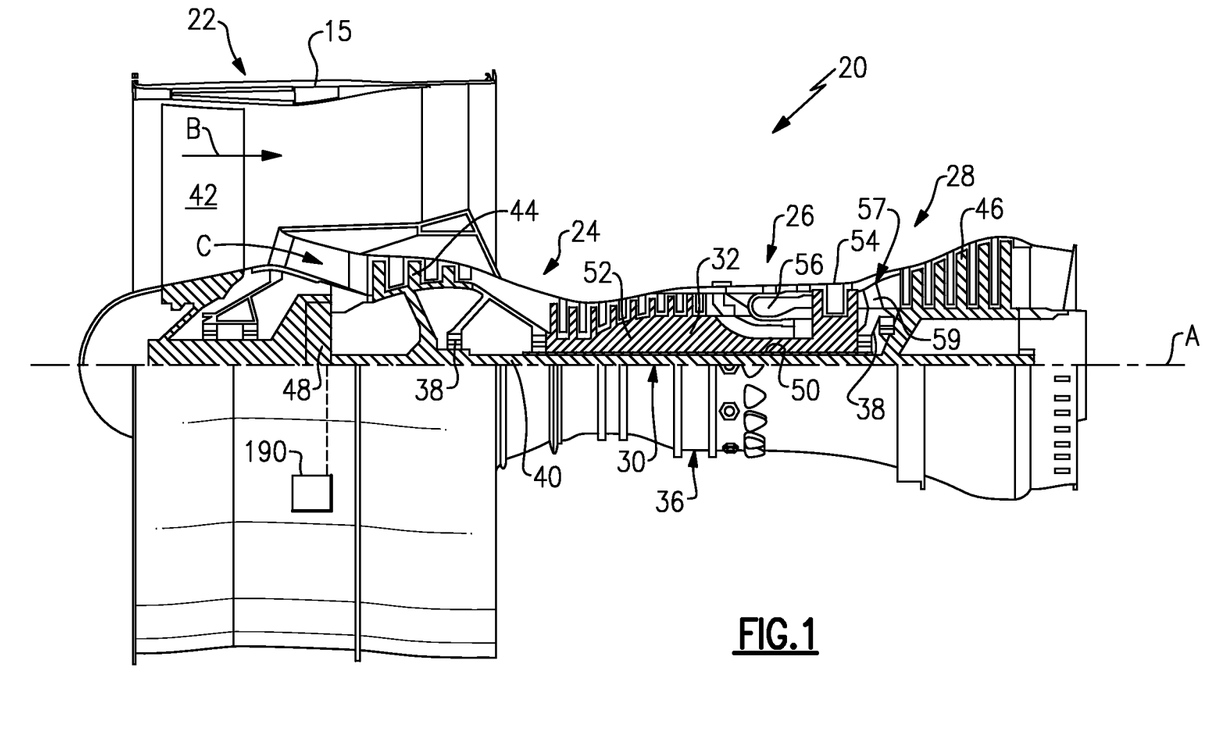
FIG. 1 schematically illustrates a gas turbine engine.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct defined within a nacelle 15, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The exemplary engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a first (or low) pressure compressor 44 and a first (or low) pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a second (or high) pressure compressor 52 and a second (or high) pressure turbine 54. A combustor 56 is arranged in exemplary gas turbine 20 between the high pressure compressor 52 and the high pressure turbine 54. A mid-turbine frame 57 of the engine static structure 36 is arranged generally between the high pressure turbine 54 and the low pressure turbine 46. The mid-turbine frame 57 further supports bearing systems 38 in the turbine section 28. The inner shaft 40 and the outer shaft 50 are concentric and rotate via bearing systems 38 about the engine central longitudinal axis A which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The mid-turbine frame 57 includes airfoils 59 which are in the core airflow path C. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, gear system 48 may be located aft of combustor section 26 or even aft of turbine section 28, and fan section 22 may be positioned forward or aft of the location of gear system 48.

The engine 20 in one example is a high-bypass geared aircraft engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present invention is applicable to other gas turbine engines including direct drive turbofans.

A significant amount of thrust is provided by the bypass flow B due to the high bypass ratio. The fan section 22 of the engine 20 is designed for a particular flight condition—typically cruise at about 0.8 Mach and about 35,000 feet (10,668 meters). The flight condition of 0.8 Mach and 35,000 ft (10,668 meters), with the engine at its best fuel consumption—also known as "bucket cruise Thrust Specific Fuel Consumption ('TSFC')"—is the industry standard parameter of lbm of fuel being burned divided by lbf of thrust the engine produces at that minimum point. "Low fan pressure ratio" is the pressure ratio across the fan blade alone, without a Fan Exit Guide Vane ("FEGV") system. The low fan pressure ratio as disclosed herein according to one non-limiting embodiment is less than about 1.45. "Low corrected fan tip speed" is the actual fan tip speed in ft/sec divided by an industry standard temperature correction of $[(\text{Tram }° \text{ R})/(518.7° \text{ R})]^{0.5}$. The "Low corrected fan tip speed" as disclosed herein according to one non-limiting embodiment is less than about 1150 ft/second (350.5 meters/second).

The geared architecture 48 includes one or more components (e.g., journal pins 90) having a non-ferrous metal coating. A lubrication system 150 (see FIG. 3) lubricates the geared architecture, and includes a non-ferrous chip detector 190 situated downstream of the geared architecture 48. As shown in FIG. 1, the non-ferrous chip detector 190 may be situated towards a front of the gas turbine engine 20. If the non-ferrous chip detector 190 detects a threshold amount of non-ferrous metal debris, engine controller 214 may infer that the one or more components having the non-ferrous metal coating are spalling due to a lack of lubricant (see FIG. 5). The non-ferrous chip detector 190 is located downstream of the geared architecture 48, but upstream of a scavenge pump 156 in the lubrication system 150 (see FIG. 4).

Figure 2A:
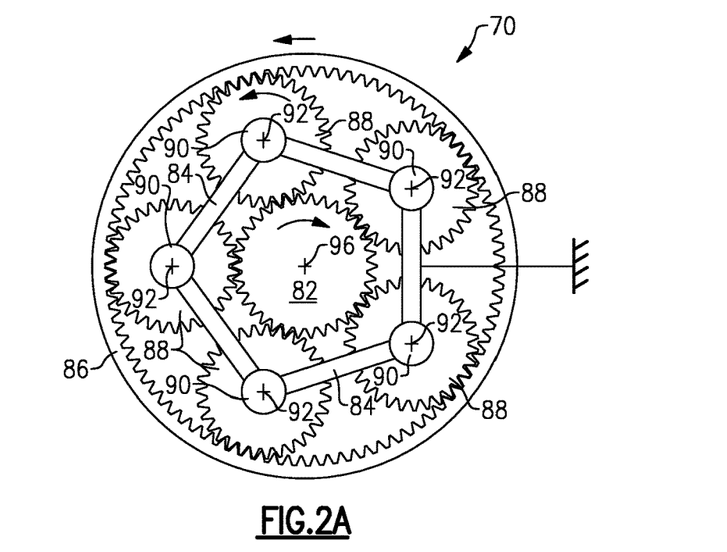
FIG. 2A schematically illustrates an example epicyclic gear train that may be used in the gas turbine engine of FIG. 1.

FIG. 2A schematically illustrates a view of an example epicyclic gear train 70 that may be used as part of the geared architecture 48. The gear train 70 includes a sun gear 82, a ring gear 86 radially outboard of the sun gear 82, and a set of intermediate gears 88 radially intermediate and meshing with the sun gear 82 and ring gear 86. Each intermediate gear 88 rotates about a respective axis 92 of its associated journal pin 90. In one or more embodiments, the axes 92 are parallel with each other and with the axis A of FIG. 1, but are non-coaxial with the axis A of FIG. 1. Lubricant is supplied from manifold 100 through passages 106 to the journal pins 90. Lubricant recovery gutter 120 surrounds the gear system 70 and captures lubricant expelled from the journal pins 90 and intermediate gears 88.

Each journal pin 90 has a non-ferrous metallic coating. The non-ferrous metallic coating in some embodiments can include copper, silver, lead, for example. In some embodiments, a non-ferrous metal alloy can be used. A thin film of lubricant 93 occupies a small annular space 94 between each intermediate gear 88 and its journal pin 90 to support rotation of the intermediate gear 88 about the journal pin 90 as a journal bearing. An example journal bearing 95 is shown in FIG. 2A. The journal pins 90 are located within the intermediate gears 88 and extend between opposing sides of a carrier 84.

Figure 3:
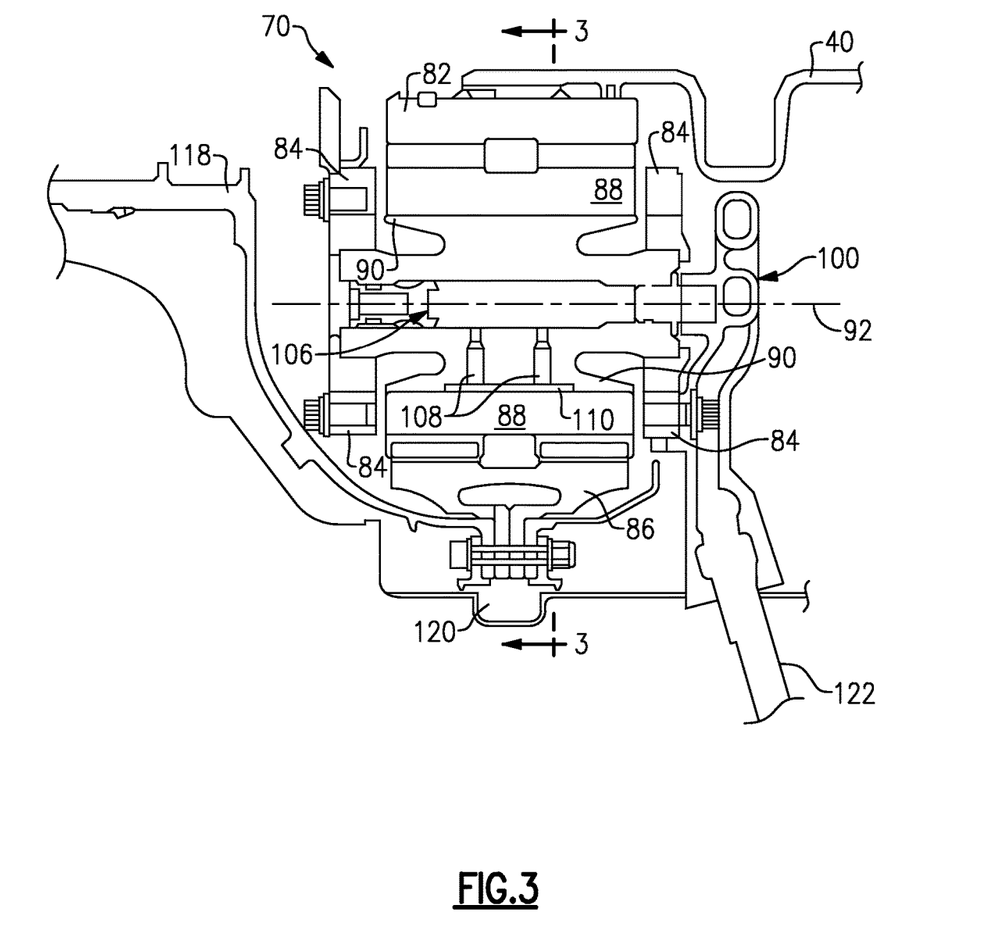
FIG. 3 schematically illustrates another view of the gear train and journal pin of FIGS. 2A-B.

FIG. 3 illustrates an example schematic cross-sectional view of the epicyclic gear train 70 of FIG. 2A (and FIG. 2A is a view of the gear train 70 taken along line 3-3 of FIG. 3). FIG. 3 is a cross-sectional view of the epicyclic gear train 70 taken through only a single intermediate gear 88. Epicyclic gear train 70, however, includes multiple intermediate gears 88 arranged circumferentially around the sun gear 82 as shown in FIG. 2A. In addition to intermediate gear 88, ring gear 86, and sun gear 82, the epicyclic gear train 70 includes journal pins 90, a lubricant manifold 100, and carrier 84. The carrier 84 is stationarily mounted within gas turbine engine 20 to the non-rotating engine case walls radially outboard of epicyclic gear train 70. The carrier 84 has two generally interfacing faces that support the ends of the journal bearing 95 of journal pin 90. The carrier 84 is disposed adjacent the rotatable intermediate gear 88 and sun gear 82. The sun gear 82 is rotatably mounted on the low pressure, inner shaft 40. Journals pin 90 includes axial passage 106 and radial passages 108. Radial passages 108 fluidly connect to the distribution recess 110. Lubricant manifold 100 is connected to feed tube 122.

The lubricant manifold 100 is disposed adjacent to the journal pin 90 and is fluidly connected thereto. Axial passage 106 is fluidly connected to lubricant manifold 100. Lubricant manifold 100 is fed lubricant from other components of the gas turbine engine via feed tube 122. The lubricant from lubricant manifold 100 is supplied through axial passage 106 to radial passages 108. The lubricant flows through radial passages 108 into the distribution recess 110 between the journal pin 90 and the intermediate gear 88. The distribution recess 110 may extend along the outer radial surface of journal pin 90. The liquid lubricant forms a lubricant film 93 (see FIG. 2B) on the journal pin 90 in the distribution recess 110 as part of the journal bearing 95. From distribution recess 110, the lubricant film spreads circumferentially and axially due to viscous forces between intermediate gear 88 and journal pin 90. The lubricant film helps to support intermediate gear 88 and reduce friction between intermediate gear 88 and the journal pin 90 as the intermediate gear 88 rotates. A lubricant recovery gutter 120 circumscribes the ring gear 86.

Figure 2B:
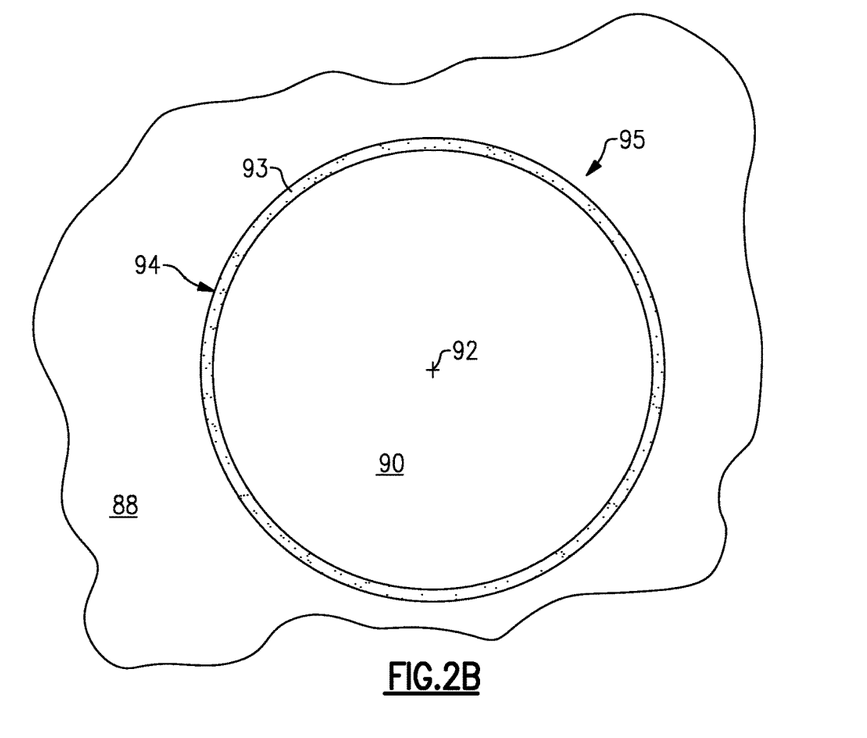
FIG. 2B schematically illustrates an example journal pin and associated journal bearing from the gear train of FIG. 2.

The example of FIGS. 2A-B and 3 depict a stars system in which the sun gear 82 and ring gear 86 are each rotatable about an axis 96 in opposing directions, but the carrier 84 is non-rotatable. However, it is understood that this is only an example, and that the teachings discussed herein could be applied to a planetary system in which the carrier 84 rotates (e.g., in a same direction as the sun gear 82), but the ring gear 86 is non-rotatable.

Figure 4:
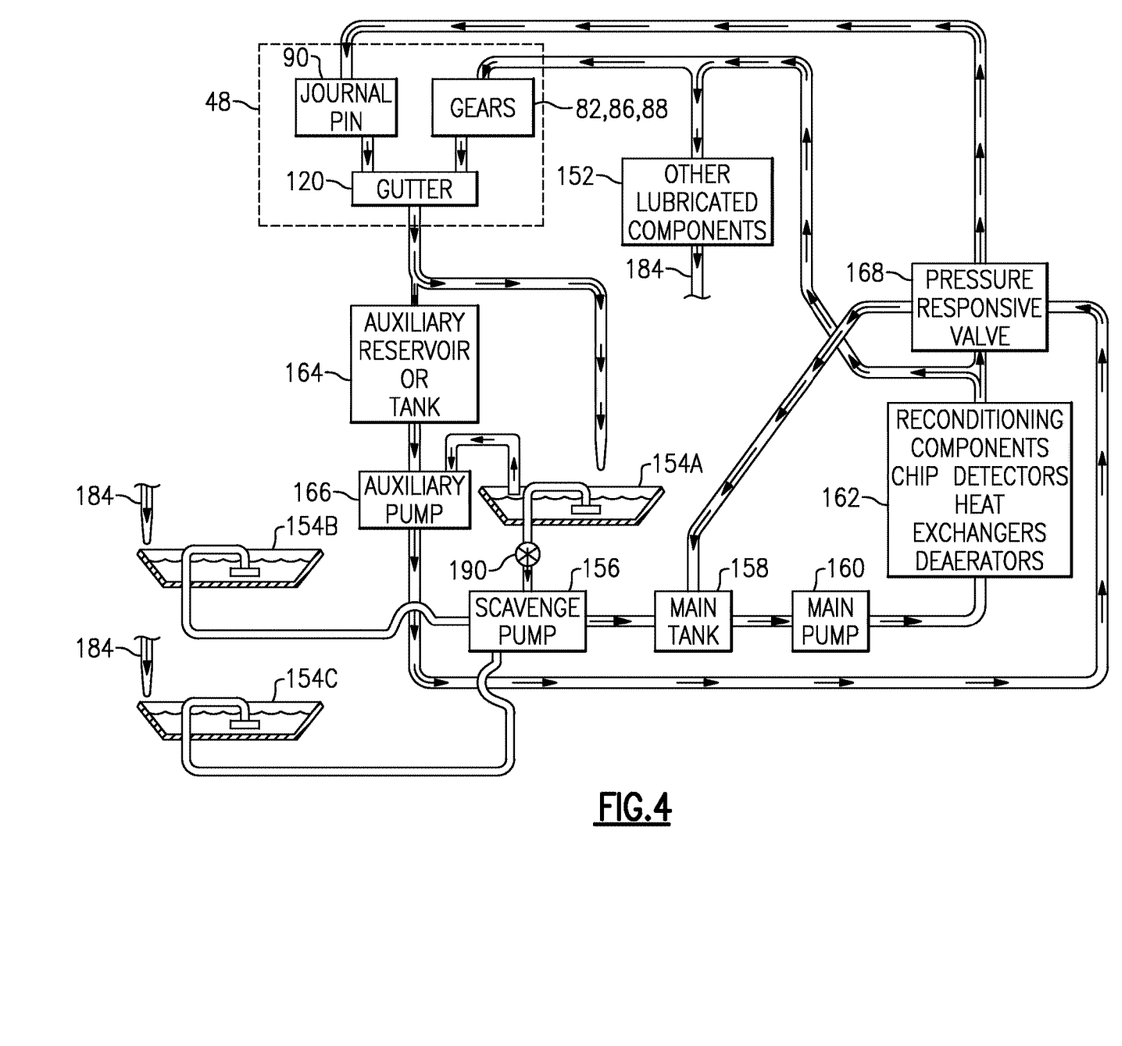
FIG. 4 schematically illustrates a lubrication system for a gas turbine engine.

Lubricant flows through the gear train 70 and also to the respective journal bearing 95 of each journal pin 90. Lubricant also flows to various gears in the gear train 70, which lubricates and cool their teeth. It is desirable to maintain the film of lubricant 93 of each journal bearing 95 at a certain thickness when rotation of the gear 88 about the journal pin 90 of the journal bearing 95 exceeds a certain speed threshold. If that thickness is not maintained, spalling of the non-ferrous metal coating of the journal pin 90 may occur, causing non-ferrous metal debris particles to flow into the lubricant recovery gutter 120. FIG. 4 schematically illustrates an example lubrication system 150 that ensures adequate lubrication.

FIG. 4 schematically illustrates an example lubrication system 150 that lubricates a number of components in the gear train 70 that are discussed above (e.g., gears 82, 86, 88, journal pins 90, and gutter 120), and also lubricates other engine components 152 requiring lubrication (e.g., mid and rear engine bearings). The lubrication system 150 includes a main system whose components include sumps 154A-C, a scavenge pump 156 for scavenging lubricant from the sumps 154A-C, a main tank 158 for receiving lubricant from the scavenge pump 156, a main pump 160 for pumping lubricant from the main tank 158, and various lubricant reconditioning components such as chip detectors, heat exchangers and deaerators, collectively designated 162. The lubrication system also includes an auxiliary system whose components include an auxiliary lubricant tank or reservoir 164 and an auxiliary pump 166. The lubrication system also includes a pressure responsive valve 168 that connects the main lubrication pump 160 and auxiliary lubrication pump 166 back to the main tank 158. The sump 154B is a mid-bearing sump, and the sump 154C is a rear bearing sump. Each of these are located aft of the geared architecture 48, towards a rear of the gas turbine engine 20. The sumps 154B-C are situated in parallel flow paths that omit the geared architecture 48.

The main lubrication supply pump 160 is designed to be a primary source of lubrication when the gas turbine engine 20 is operating. In some examples, the main lubrication supply pump 160 operates when high speed spool 32 rotates, and the auxiliary lubrication pump 166 operates when the low speed spool 30 rotates. If the gas turbine engine 20 is off but the fan 42 is windmilling, the auxiliary lubrication pump 166 still provides lubricant to the journal bearings 95 because the low speed spool 30 rotates during windmilling. The auxiliary lubrication pump 166 may also serve as a backup to the main lubrication pump 160 for lubricating the journal bearings 95 when the gas turbine engine 20 is operating.

Rotation of the gears 82, 86, 88 expels lubricant radially outwardly into the lubricant recovery gutter 120. From the gutter 120, a larger portion of the captured lubricant flows to the sump 154A, and a smaller portion flows to the auxiliary reservoir or tank 164 to establish or replenish a reserve quantity of lubricant therein. The auxiliary pump 166 pumps lubricant from the tank 164 and sump 154A to the pressure responsive valve 168. Concurrently, the scavenge pump 156 extracts lubricant from the sump 154A and delivers it to the main tank 158. The main pump 160 pumps the lubricant from the main tank 158 to the reconditioning components 152. Most of the reconditioned lubricant then flows to the gears 82, 86, 88 and other components 152, and is then recovered in mid-bearing sump 154B, and rear bearing sump 154C (along line 184). The remainder of the reconditioned lubricant flows to the pressure responsive valve 168.

During a normal pressure condition in the lubrication system 150, the pressure responsive valve 168 directs the remainder of the reconditioned lubricant to the journal pins 90 and directs lubricant received from the auxiliary pump 166 to the main tank 158. However, if lubricant pressure drops (e.g., due to a leak, clog, or other malfunction), the pressure responsive valve 168 shunts the reserve lubricant received from the auxiliary pump 166 to the journal pins 90 to ensure that the journal pins 90 receive lubricant. Although not shown in FIG. 4, it is understood that additional lubricant conduits, lines, pathways, pumps, etc. may be used.

A non-ferrous chip detector 190 is situated downstream of the geared architecture 48, but upstream of the scavenge pump 156 (i.e., situated between a fluid outlet at the geared architecture 48 and a fluid inlet of the scavenge pump 156). Although depicted as being downstream of sump 154A in FIG. 4 (i.e., situated between a fluid outlet of the sump 154A and a fluid inlet of the scavenge pump 156), in other embodiments the non-ferrous chip-detector 190 could be upstream of the sump 154A (i.e., situated between a fluid outlet at the geared architecture and a fluid inlet of the sump 154A). The non-ferrous chip detector 190 is configured to determine whether non-ferrous metal particles are present in the lubricant flowing between gutter 120 and scavenge pump 156, which could be evidence that one or more of the journal pins 90 are spalling and are not sufficiently lubricated.

Figure 5:
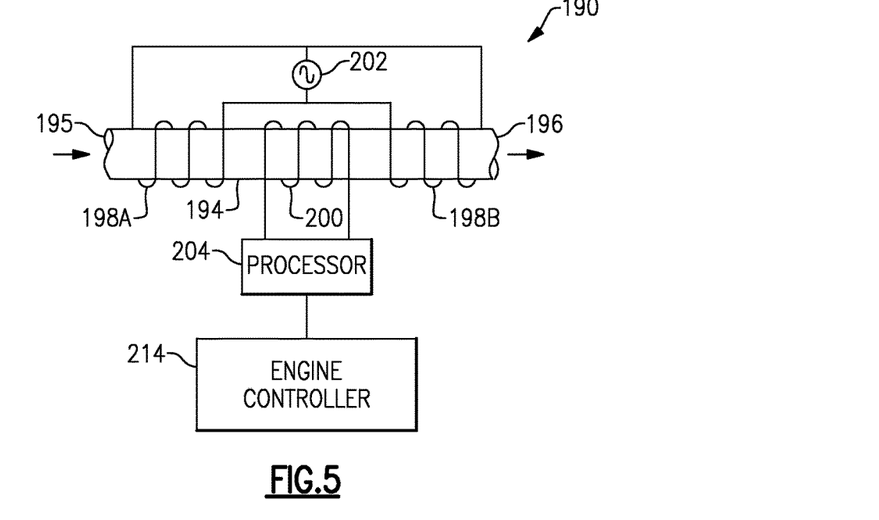
FIG. 5 schematically illustrates an example oil debris monitor (ODM).

FIG. 5 schematically illustrates an example oil debris monitor (ODM) that can be utilized as a non-ferrous chip detector 190. The non-ferrous chip detector 190 includes a lubricant conduit 194 having an inlet 195 and outlet 196. A plurality of field coils 198A-B circumferentially wrap around the conduit 194 and are configured to provide a magnetic field within the conduit 194 based on an oscillating input signal from alternating current (AC) source 202. A sense coil 200 is spaced apart from, but inductively coupled to the field coils 198A-B, and also circumferentially wraps around the conduit 194. The sense coil 200 provides an output signal based on the magnetic field from the field coils 198A-B.

Figure 6A:
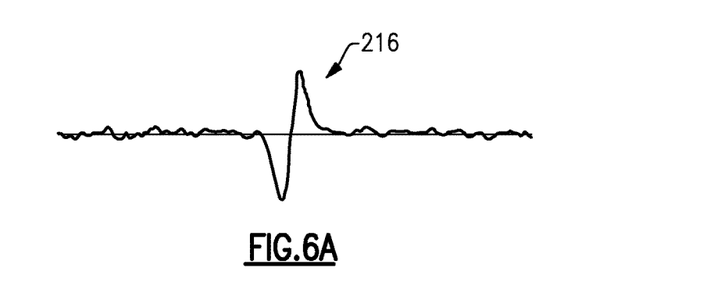
FIGS. 6A-B schematically illustrate representative signal profiles for non-ferrous and ferrous particles.
Figure 6B:
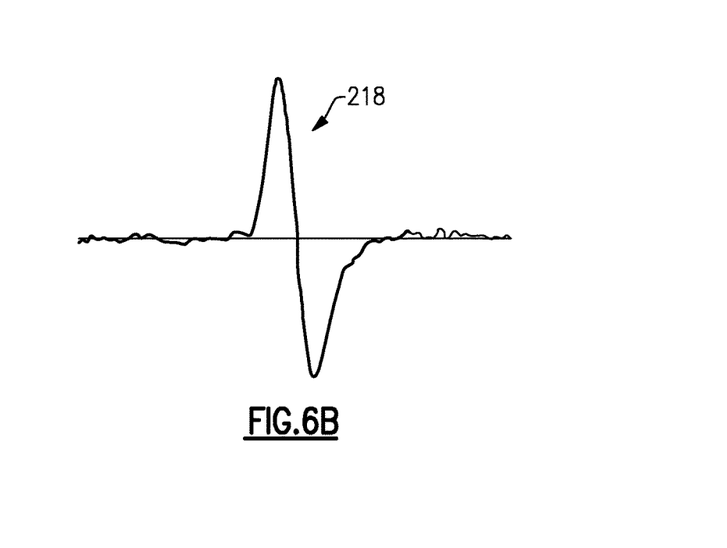

The presence of ferrous metal particles and non-ferrous metal particles affects the magnetic field within the conduit 194 provided by the field coils 198A-B. Such particles can affect the phase and/or amplitude of the output signal from the sense coil 200, for example. A processor 204 analyzes the output signal to detect whether a predefined signal profile of a non-ferrous metal particle is present in the flow of lubricant within the conduit 194. The analyzing includes comparing the output signal to a signal profile 216 of a non-ferrous metal particle (see FIG. 6A) to determine whether the output signal indicates presence of a non-ferrous particle. Optionally, the analyzing may also include comparing the output signal to a signal profile 218 of a ferrous metal particle (see FIG. 6B) to determine whether the output signal indicates a presence of a ferrous metal particle. As such, the ODM can be configured to also detect ferrous metal particles in some embodiments. Thus, the term "non-ferrous chip detector" shall not be interpreted to require omission of ferrous detection features from the chip detector 190.

The processor 204 is configured to provide a signal to an engine controller 214, which can be a Full Authority Digital Electronic Control (FADEC) or an Electronic Centralized Aircraft Monitor (ECAM), for example. The engine controller 214 is configured to determine a lubrication condition of the journal pins 90 based on the signal it receives from the processor 204, and to command a status indicator in response thereto. This determination is based on knowledge that the journal pins 90 includes a non-ferrous metal coating, and that if the journal pins 90 are deprived of lubricant, spalling of the non-ferrous metal coating may occur. Thus, evidence of such spalling may be evidence of lubrication deprivation in the journal bearings 95. The status indicator provided by the engine controller 214 could include providing a cockpit alert, and/or wirelessly transmitting a message to an airline or other entity, for example.

Figure 7:
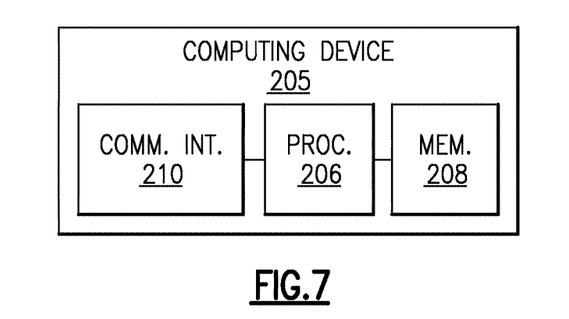
FIG. 7 schematically illustrates an example computing device that can be used in the ODM of FIG. 5.

FIG. 7 schematically illustrates an example computing device 205 that may be used as the processor 204 of FIG. 5. The computing device 205 includes processing circuitry 206, memory 208, and a communication interface 210. The memory 208 stores programs that are executed by the processing circuitry 206 for performing the methods described herein. The processing circuitry 206 may comprise a microprocessor and/or an application specific integrated circuit (ASIC), for example. The processing circuitry 206 could include multiple microprocessors or multiple cores or multiple virtual processors. The memory 208 could include any combination of electronic, magnetic, optical or even off-board storage, for example. The communication interface 210 may include an input port to support a wired data connection, or a wireless device to support a wireless connection, for example. The memory may store the signal profile 216, and optionally also the profile 218, for detecting metal debris particles in the flow of lubricant between the geared architecture 48 and the scavenge pump 156 in the lubrication system 150.

Figure 8:
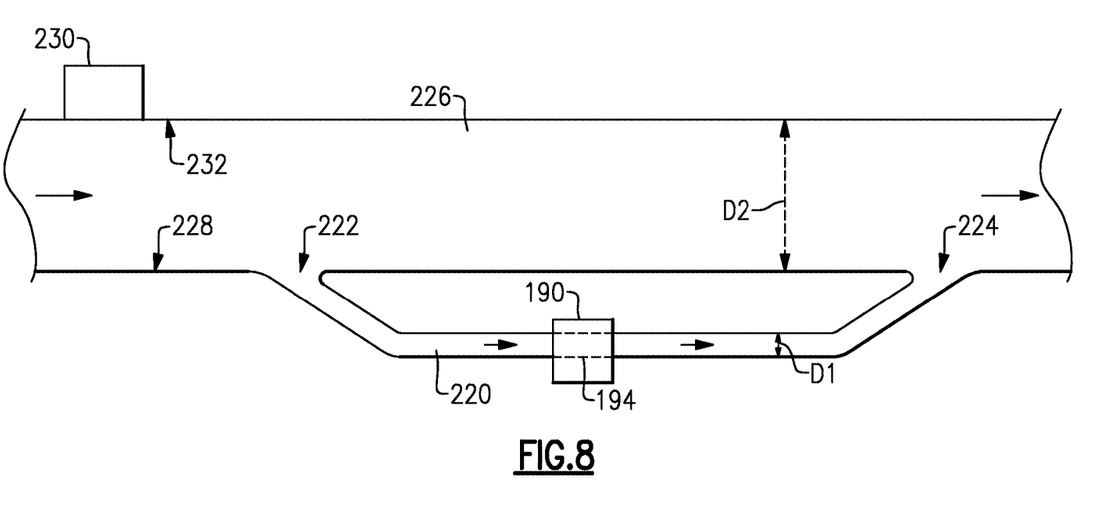
FIG. 8 schematically illustrates a bypass lubrication flow arrangement for the ODM of FIG. 5.

FIG. 8 schematically illustrates a bypass lubrication flow arrangement for the non-ferrous chip detector 190 of FIG. 5. In this example arrangement, the conduit 194 is part of a bypass 220 whose inlet 222 and outlet 224 are in fluid communication with a main conduit 226 that also carries lubricant between a fluid outlet at the geared architecture 48 and a fluid inlet of the scavenge pump 156. A diameter D1 of the bypass 220 is less than a diameter D2 of the main conduit 226. Optionally, a magnetic device 230 may be situated downstream of the geared architecture 148 but upstream of the inlet 222 to the bypass 220 (i.e., situated between a fluid outlet at the geared architecture 48 and the inlet 222), to divert ferrous particles away from the inlet 222, and make it less likely that ferrous particles will enter the bypass 220.

As discussed above, the presence of ferrous particles in a lubricant flow may make detection of non-ferrous particles more difficult. Ferrous particles have a stronger effect on the magnetic field provided by the chip detector 190, and therefore have a stronger effect on the output signal from the sense coil 200. As a result, ferrous particles are more readily detectable and could obscure the presence of non-ferrous particles, which are harder to detect. The diverting of magnetic device 230 may reduce the likelihood that ferrous particles would be present in the lubricant being analyzed for non-ferrous particles. In one or more embodiments, the magnetic device 230 is an electromagnetic device that can be activated and deactivated. In the same or other embodiments, the magnetic device 230 at least partially wraps around a side 232 of the main conduit 226 that is opposite from a side 228 at which the inlet 222 and outlet 224 connect.

Optionally, the non-ferrous chip detector 190 may be situated at a line-replaceable location that can be accessed through removal of nacelle 15 (see FIG. 1), and possibly also some degree of wiring harness removal. Situating the non-ferrous chip detector 190 towards the front of the gas turbine engine 120 can avoid costly rear engine component removal in some embodiments.

Figure 9:
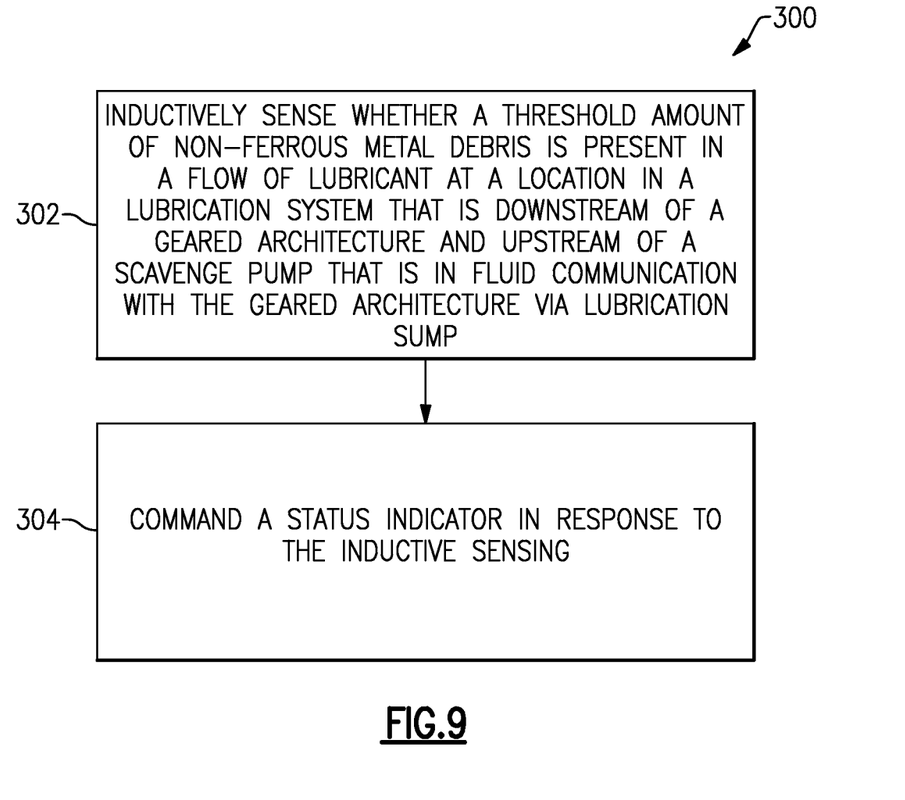
FIG. 9 is a flowchart of an example method.

FIG. 9 is a flowchart of an example method 300. The method 300 includes inductively sensing (block 302) whether a threshold amount of non-ferrous metal debris is present in a flow of lubricant at a location in lubrication system 150 that is downstream of a geared architecture 48 and upstream of a scavenge pump 156 (i.e., between a fluid outlet at the geared architecture 48 and a fluid inlet of the scavenge pump 156) (block 302). The scavenge pump 156 is in fluid communication with the geared architecture 48 via a lubrication sump 154A. In one example, the conduit connects gutter 120 to sump 154A (such that the location is upstream of the lubrication sump 154A). In another example, the conduit connects sump 154A to scavenge pump 156 (such that the location is downstream of the lubrication sump 154A). The method 300 also includes commanding a status indicator in response to the inductive sensing (block 304). The status indicator could comprise a cockpit alert for a pilot, and/or wirelessly transmitting a message to an airline or other entity, for example.

In one example, the method 300 also includes diverting lubricant from a main conduit 226 that carries lubricant between a fluid outlet at the geared architecture 48 and a fluid inlet of the scavenge pump 156 into a bypass 220 whose inlet 222 and outlet 224 are in fluid communication with the main conduit 226. In this example, the location at which the inductive sensing is performed is in the bypass 220 (as shown in FIG. 8).

In one example, the method 300 also includes providing a magnetic field downstream of the geared architecture 48 but upstream of the inlet 222 to the bypass 220, to divert ferrous particles away from the inlet 222. This could improve the accuracy of the non-ferrous chip detector 190 in some embodiments, as non-ferrous metal particles may be more difficult to detect than ferrous ones, as their effect on a magnetic field provided by the non-ferrous chip detector 190 may be weaker.

In one example, the inductive sensing of block 302 includes passing an oscillating input signal through at least one field coil 198 to provide a magnetic field within a conduit of lubrication system 150, and obtaining an output signal based on the magnetic field from a sense coil 200 that is spaced apart from, but inductively coupled to the at least one field coil 198. The method also includes analyzing the output signal to detect whether non-ferrous metal debris is present at the location in the conduit based on a predefined signal profile 216 of a non-ferrous metal particle.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A gas turbine engine, comprising:
   a turbine operatively connected to a fan rotor through a geared architecture that provides a gear reduction, the geared architecture having a journal pin with a non-ferrous metal coating;
   a lubricant system for the geared architecture and having an outlet at the geared architecture;
   a scavenge pump having a fluid inlet in fluid communication with the outlet at the geared architecture;
   a non-ferrous chip detector situated between the outlet at the geared architecture and the fluid inlet of the scavenge pump, wherein the non-ferrous chip detector is further situated between a lubrication sump downstream of the outlet and the fluid inlet of the scavenge pump, such that fluid exiting the outlet will pass through the lubrication sump, and then pass through the non-ferrous chip detector before arriving at the fluid inlet; and
   a controller configured to determine a lubrication condition of the journal pin based on a signal received from the non-ferrous chip detector, and command a status indicator in response thereto.

2. The gas turbine engine of claim 1, wherein the non-ferrous metal coating comprises one or more of copper, silver, and lead.

3. The gas turbine engine of claim 1, wherein the scavenge pump is operative to pump lubricant from the lubrication sump, and from one or more additional lubrication sumps that are located in parallel flow paths that omit the geared architecture.

4. The gas turbine engine of claim 1:
   wherein the non-ferrous chip detector at least partially surrounds a portion of conduit that carries lubricant between the outlet at the geared architecture and the fluid inlet of the scavenge pump; and
   wherein the portion of conduit is a bypass whose inlet and outlet are in fluid communication with a main conduit that also carries lubricant between the outlet at the geared architecture and the fluid inlet of the scavenge pump, the bypass having a smaller diameter than a diameter of the main conduit.

5. The gas turbine engine of claim 4, wherein the non-ferrous chip detector comprises:
- at least one field coil configured to provide a magnetic field based on an oscillating input signal;
- a sense coil that is spaced apart from, but inductively coupled to the at least one field coil, and is configured to provide an output signal based on the magnetic field; and
- a sensor that is electrically coupled to the sense coil, and is configured to detect a presence of non-ferrous particles in the portion of conduit based on the output signal and a predefined signal profile of a non-ferrous metal particle.

6. The gas turbine engine of claim 5, wherein the at least one field coil and the sense coil wrap circumferentially around the portion of conduit.

7. The gas turbine engine of claim 6, wherein the at least one field coil comprises a first field coil upstream of the sense coil, and a second field coil downstream of the sense coil.

8. The gas turbine engine of claim 4, comprising:
- a magnetic device situated between the outlet at the geared architecture and the inlet to the bypass, and operative to divert ferrous particles away from the inlet to the bypass.

\* \* \* \* \*